United States Patent

Yamashita et al.

[11] Patent Number: 6,004,786
[45] Date of Patent: Dec. 21, 1999

[54] INORGANIC CARRIER CONTAINING BOUND SILANE COUPLING AGENT HAVING CARBOXYLIC-ESTER GROUP FOR IMMOBILIZING LIPASE

[75] Inventors: Yoshitaka Yamashita; Masanobu Kamori; Hideo Takenaka, all of Kochi; Joji Takahashi, Tama, all of Japan

[73] Assignee: Toyo Denka Kogyo Co., Ltd., Japan

[21] Appl. No.: 08/847,512

[22] Filed: Apr. 24, 1997

[30] Foreign Application Priority Data

May 28, 1996 [JP] Japan ..................................... 8-157619

[51] Int. Cl.$^6$ ........................... C12N 11/14; C12N 11/06; C12P 7/64
[52] U.S. Cl. ........................... 435/176; 435/134; 435/181
[58] Field of Search ..................................... 435/134, 176, 435/181

[56] References Cited

U.S. PATENT DOCUMENTS 4,384,045  5/1983  Ho et al. .................................. 435/176
4,415,631  11/1983  Schutijser .................................. 428/405

FOREIGN PATENT DOCUMENTS

| 55-32357 | 8/1980 | Japan . |
| 56-15231 | 4/1981 | Japan . |
| 451894 | 2/1992 | Japan . |
| 5219952 | 8/1993 | Japan . |
| 9005778 | 5/1990 | WIPO . |

*Primary Examiner*—David M. Naff
*Attorney, Agent, or Firm*—Joseph W. Berenato, III

[57] ABSTRACT

A carrier for immobilizing lipase is prepared by bonding a silane coupling agent having a carboxylic-ester group to an inorganic carrier. Preferred silane coupling agents are γ-methacryl oxypropyltrimethoxy silane, γ-acetoxypropyltrimethoxy silane or γ-acryloxypropyltrimethoxy silane. The inorganic carrier can be kaolinite, porous glass, bentonite, silica gel, alumina, silica, silica-alumina hydroxy apatite or calcium phosphate gel. Lipase is immobilized by mixing lipase with the inorganic carrier containing the bound silane coupling agent, filtering the resultant mixture and drying the filtered mixture. Functional groups of the lipase are bonded to the carboxylic-ester group of the silane coupling agent.

6 Claims, 2 Drawing Sheets

INORGANIC CARRIER CONTAINING BOUND SILANE COUPLING AGENT HAVING CARBOXYLIC-ESTER GROUP FOR IMMOBILIZING LIPASE

BACKGROUND OF THE INVENTION

1. Field of the Invention

The present invention generally relates to enzyme immobilizing carriers and immobilized lipase which are used as a bioreactor, biosensor, and so on to facilitate various biochemical reactions in an industrial field wherein various enzymes are employed as a biological catalyst.

2. Description of the Prior Art

In order to execute various biochemical reactions in an industrial field by using an organic catalyst, for example, an enzyme catalyst, many researches and studies on an immobilized enzyme bioreactor and a biosensor have been actively carried out in recent years. On the same occasion, studies on a carrier for immobilizing enzyme; i.e., an enzyme immobilizing carrier, which is applied to these bioreactor and biosensor, have also been developed. This immobilized enzyme bioreactor includes a column which is filled with an organic catalytic material made of an immobilized enzyme carrier. For the carrier, various materials may be used, for example, high molecular organic materials and inorganic materials such as commonly used porous glass, ceramics, and so on.

Although such inorganic materials have some advantages such as a high mechanical strength, and an excellent thermal and chemical stability during a sterilization treatment, they have the disadvantage that they cannot be repeatly used, due to a poor adsorption force for enzymes. Some conventional arts have been proposed to overcome such adisadvantage. For example, Japanese Patent Publication No.55-32357 and No.56-15231 disclose one typical process where an amount of silane coupling agent introduced with reactive organic radicals are combined with an inorganic carrier such as porous glass, alumina, silica, and so on, and then the enzyme's functional groups are reacted with the reactive organic radicals of the silane coupling agent to realize bonding between the inorganic carrier and the enzyme.

As a typical example of such enzyme immobilized in the inorganic carrier (hereinafter, referred to "immobilized enzyme") including the silane coupling agent, carbohydrate-decomposing enzymes such as α-amylase, glucoamylase, and so on are known. However, since these enzymes have a low activity; i.e., a poor reactivity with starch or other substrates, compared to the enzyme not immobilized in carrier, a great amount of the immobilized enzyme is required to obtain the same level of reactivity in a non-immobilized enzyme. Accordingly, the immobilized enzyme is not adapted for a producing process in an industrial field. In order to overcome this problem, Japanese Patent Publication No. 5-219952 and 4-51894 disclose a novel carrier and method for immobilizing enzyme into the carrier.

On the other hand, one of typical fat splitting enzyme, lipase, has been rapidly and widely used for various techniques in the field of organic synthesis chemistry such as monoester decomposition, ester synthesis, optical resolution of racemic modification by ester exchange reaction, and so on which is like a splitting function on oil and fat. Nevertheless, it has been only studied and developed as an industrial immobilizing method to physically adsorb a high concentrated lipase solution into diatomaceous earth. In order to produce lipase-adsorbed diatomaceous earth, it is necessary to mix the high concentrated solution of coarse enzymic lipase with diatomaceous earth and then dry the mixture. However, the physical adsorbability of the diatomaceous earth is limited and its adsorbing force is relatively low owing to the physical adsorption. Accordingly, the activity of the lipase-adsorbed diatomaceous earth will gradually decrease by repetition.

Primarily, a main object of using the immobilized enzyme is that although the enzyme is expensive, it can be repeatly used without disposal after only one usage, therefor decreasing production cost and the reacted product is free from any remaining enzymes. In other words, it is desirable to realize a specific immobilized enzyme which can be repeatedly used for a long period with the smallest amount possible. As the activity of immobilized enzyme is increased, a scale of reaction apparatus becomes smaller thereby providing the merit of lowering its initial and running cost.

BRIEF SUMMARY OF THE INVENTION

Therefore, it is an objective of the present invention to provide an improved inorganic carrier for immobilizing enzyme, which overcomes the above described conventional problems.

Another objective of the present invention is to provide an improved inorganic carrier for immobilizing enzyme, which facilitates to immobilize lipase.

An additional objective of the present invention is to provide an immobilized lipase which has a high activity.

A further objective of the present invention is to provide an inorganic immobilized enzyme and immobilized lipase which can be repeatly used and at the same time hardly lowering its activity.

To accomplish the above described objectives, an improved inorganic carrier is produced by combining inorganic carrier with the coupling agent having carboxylic-ester linkage, and an improved inorganic carrier for carrying lipase is produced by combining inorganic carrier with the coupling agent having carboxylic-ester linkage. The coupling agent having carboxylic-ester linkage is a silane coupling agent. The inorganic carrier is selected from kaolinite type carriers for immobilizing enzyme or any carriers, having the functional group capable of bonding to silane coupling agent, such as porous glass, bentonite, silica gel, alumina, silica, silica-alumina hydroxy apatite, calcium phosphate-gel, and so on.

The silane coupling agent having carboxylic-ester linkage is selected from the coupling agents having carboxylic-ester linkage which are represented by a general formula RCOO(CH$_2$)nSiR'$_3$ (wherein "R" represents an organic functional group, "R'" represents a radical selected from the group including lower alkoxy, phenoxy, and halogen; and "n" represents an integral number). For example, γ-methacryl oxypropyltrimethoxy silane, γ-acetoxypropyltrimethoxy silane, γ-acryloxypropyltrimethoxy silane, etc. can be used.

Furthermore, the present invention provides an immobilized lipase in which functional groups contained in lipase protein are bonded to carboxylic-ester in the following steps; the first step is for combining inorganic carrier with the coupling agent having carboxylic-ester linkage, the second step is for mixing and stirring the inorganic carrier resulting from the first step with a lipase solution having a predetermined concentration, the third step is for filtering the mixture, and the fourth step is for drying the filtered material.

Such improved inorganic carriers for immobilizing enzyme and immobilized lipase provide extraordinary advantages. In detail, the carrier and immobilized lipase produced by the present invention have an extremely high activity even though the amount of protein adsorbed to the carrier is not as much as in the conventional manner where lipase is carried with other carriers combined with the silane coupling agents having no carboxylic-ester linkage or non-treated carriers. In other words, the carrier and immobilized lipase produced by the present invention have a relative extremely high activity to the amount of protein adsorbed to the carrier and an extremely low deterioration during the activity. Furthermore, the process provided by the present invention to bond the functional groups contained in lipase protein to carboxylic-ester does not need a complicated immobilizing treatment, but only ordinarily immobilizing steps wherein the lipase solution having a predetermined concentration is mixed and stirred with carrier, and then the mixture is subjected to filtering and drying. The produced carrier and immobilized lipase can be repeatedly used with hardly lowering its activity. Particularly, in repeated batch-reaction process, the produced carrier and immobilized lipase according to the present invention can be advantageously used, free from lowering their activity.

DETAILED DESCRIPTION OF THE PREFERRED EMBODIMENT

Figure 1:
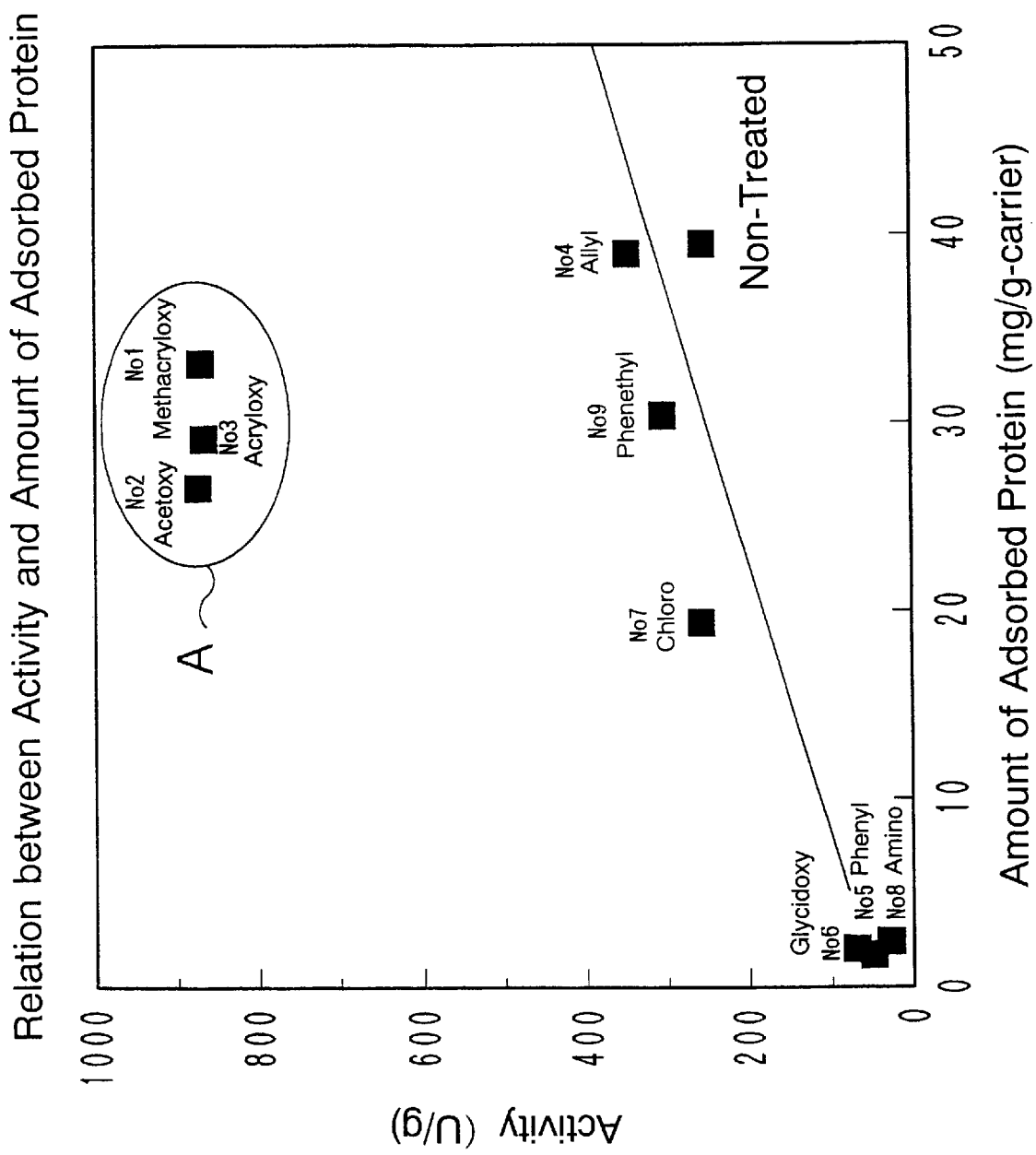
FIG. 1 is a graphical representation which shows the relation between the initial activity and the amount of protein adsorbed to the carrier of the embodiment of the present invention and that of the comparative example and non-treated carrier.

The present invention will be understood by discussing about a preferred embodiment of carrier for immobilizing enzyme and immobilized lipase produced by using the carrier. According to the present invention, it is characterized that an inorganic carrier is combined with the coupling agent having carboxylic-ester linkage, and the carrier for carrying lipase is produced by combining the coupling agent having carboxylic-ester linkage with an inorganic carrier.

Table 1 shows various coupling agents to be used in the present invention and their structural formulae.

TABLE 1

Structural Formulae of Coupling Agents

| No. | Name of Coupling Agent | Functional Group (X—) |
|---|---|---|
| 1 | γ-methacryl oxypropyltrimethoxy silane | 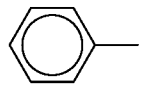 |
| 2 | γ-acetoxypropyltrimethoxy silane | $CH_3-\overset{\overset{O}{\|}}{C}-O-$ |

TABLE 1-continued

Structural Formulae of Coupling Agents

| No. | Name of Coupling Agent | Functional Group (X—) |
|---|---|---|
| 3 | γ-acryloxypropyltrimethoxy silane | $CH_2\!=\!CH-\overset{\overset{O}{\|}}{C}-O-$ |
| 4 | allyltrimethoxy silane | $CH_2\!=\!CH-$ |
| 5 | phenyltrimethoxy silane | 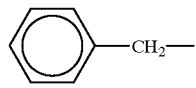 |
| 6 | γ-glycidoxypropyltrimethoxy silane | $CH_2\!-\!CHCH_2O-$ with epoxide O |
| 7 | γ-chlorupropyltrimethoxy silane | Cl— |
| 8 | γ-aminopropyltrimethoxy silane | $NH_2-$ |
| 9 | phenethyltrimethoxy silane | phenyl—$CH_2-$ |

General Structural Formula: $X-(CH_2)n-Si(OCH_3)_3$ (n=0~3)

In Table 1, No. 1 to No. 3 represent the silane coupling agents having carboxylic-ester linkage which are employed in the present invention, while No. 4 to No. 9 represent the other silane coupling agents as comparative examples. In detail, the present invention employs the coupling agents having carboxylic-ester linkage which are preferably selected from the silane coupling agents represented by a general formula; $RCOO(CH_2)nSiR'_3$. In this formula, "R" represents an organic functional group which may include an inorganic functional group at the end. "R'" represents a radical selected from the group including lower alkoxy, phenoxy, and halogen. "n" represents an integral number.

The inorganic carrier to be used in the present invention is selected from kaolinite type carriers for immobilizing enzyme or any carriers, having the functional group capable of bonding to silane coupling agent, such as porous glass, bentonite, silica gel, alumina, silica, silica-alumina hydroxy apatite, calcium phosphate-gel, and so on.

In the following embodiments of the present invention, the kaolinite-type carrier for immobilizing enzyme, formed in particle having an average diameter of 200 μm, was used to combine various silane coupling agents onto the surface of the carrier, and then to make the carrier carry lipase. Thus produced carrier examples were subjected to various tests to compare their reaction activities. The result of these tests clearly indicated that the samples based on No. 1 to No. 3 had higher activity than the conventional samples based on No. 4 to No. 9 even though the amount of protein adsorbed to the carriers produced by the present invention was not especially large. In detail, the carrier combined with the silane coupling agent having carboxylic-ester linkage selected from γ-methacryl oxypropyltrimethoxy silane, γ-acetoxypropyltrimethoxy silane and γ-acryloxypropyltrimethoxy silane was used to carry lipase, (hereinafter, this is referred to as "ester-combined immobilized lipase). On the other hand, the carrier combined with the other silane coupling agent having no carboxylic-ester linkage was used to carry lipase, (hereinafter, this is referred to as "other silane coupling immobilized lipase").

The above described kaolinite-type carrier for immobilizing enzyme was produced by a process wherein a kaolin mineral is subjected to a hydrothermal treatment with a strong acid, a rinsing treatment with water to form a slurry or powdery material, and a baking treatment at a temperature of 350° C. to 1000° C. Thus produced kaolinite-type carrier which has a sharp and uniform porous distribution, and a high porous-ratio.

The above described kaolinite-type carrier producing process provides some advantages. The hydrothermal treatment with a strong acid makes alkaline components included in the kaolin mineral as impurities are dissolved out of it, so that the slurry or powdery material through the hydrothermal treatment does not almost include soluble alkaline components. As a result, the chemical stability inherently belonging to the kaolin mineral is remarkably improved.

It is noted that in the case of the carrier combined with γ-aminopropyltrimethoxy silane (No. 8 in Table 1) which is known as highly effective for the other enzymes except for lipase, such carrier immobilizes a small amount of lipase and the immobilized carrier has a low activity.

Generally, since commercially available lipase includes much coase enzyme powder which also includes various protein materials in addition to pure lipase protein, it is impossible to selectively carry such pure lipase protein component on the carrier. Therefore, in order to increase the activity it is necessary to make a large amount of highly concentrated coarse enzymic lipase to adsorb a great amount of protein onto the carrier. This will result in difficult immobilizing operation and also requires the carrier having an extremely high adsorbability. On the contrary, when the carrier combined with the silane coupling agent having carboxylic-ester linkage is used, it is possible to produce the immobilized lipase having a remarkably high activity even though the carrier is not adsorbed with a great amount of protein.

Accordingly, the present invention does not require the above described conventional difficult immobilizing process to produce lipase-adsorbed diatomaceous earth, in which it is necessary to mix the highly concentrated solution of coarse enzymic lipase with diatomaceous earth and then dry the mixture, but requires only a commonly used immobilizing process; i.e., the carrier is mixed and stirred with a lipase solution having a predetermined concentration, and the mixture is filtered and dried. Although the reason of this phenomenon is not completely understood, it can be anticipated as follows. It is well known that enzyme is a specific protein acting as a biological catalyst and its 20 kinds amino acid residues have various functional groups such as amino group, carboxyl group, and so on. In the case of lipase protein, any one of these functional groups is easily bonded to carboxylic-ester so that lipase protein can be selectively bonded to the carboxylic-ester of carrier rather than the other proteins.

The comparative tests for comparing the deterioration of activity during repetition indicate that the ester-linkage immobilized lipase according to the present invention have a strong adsorbing force which results in a high activity with extremely low deterioration in comparison with the other immobilized lipase samples which are produced by using the other silane coupling agents or without silane coupling agent.

To easily understand the present invention, a typical embodiment will be described as follows.

Embodiment

As an example of reaction for optical resolution of racemic modification, DL-1-phenethyl alcohol was mixed with vinyl acetate as an acyl donor to perform the esterification of racemic modification with lipase as catalyst. The used lipase was a lipase PS (Pseudomonas cepacia originated by Amano Seiyaku Co.,Ltd.) which was already conformed that this lipase PS can perform selectively catalytic reaction of racemic modification, especially for the above described reaction, the lipase PS indicates an extremely high selectivity. The lipase PS immobilized carrier was used.

EXAMPLES 1 to 3

Each of the silane coupling agents, No. 1 to No. 3 in Table 1, having carboxylic-ester linkage, 0.2 g, was diluted by toluene, 1.8 g. Kaolinite type carrier for immobilizing enzyme, 1.5 g, was added into the toluene diluted silane coupling agent solution, and mixed for one hour. The solution was separated into solid part and liquid part. The solid part was dried at 110° C. for 30 min. Thus the carrier material was produced.

Then coarse enzymic lipase (lipase PS manufactured by Amano Seiyaku Co.,Ltd.), 2.5 g, was solved in phosphoric acid buffer (pH 7.0), 25 ml. This solution was filtered to remove insoluble materials. The above prepared carrier, 0.5 g, was added into this enzyme solution, and this mixture was shaken for one day to produce immobilization. Finally, this mixture was filtered to recover the immobilized lipase.

COMPARATIVE EXAMPLES 4 to 9

Each of the silane coupling agents No. 4 to No. 9 shown in Table 1, 0.2 g, was diluted by toluene, 1.8 g. Kaolinite type carrier for immobilizing enzyme, 1.5 g, was added into the toluene diluted silane coupling agent solution, and mixed for one hour. The solution was separated into solid part and liquid part. The solid part was dried at 110° C. for 30 min. Thus the carrier material was produced.

Then coarse enzymic lipase (lipase PS manufactured by Amano Seiyaku Co.,Ltd.), 2.5 g, was solved in phosphoric acid buffer (pH 7.0), 25 ml. This solution was filtered to remove insoluble materials. The above prepared carrier, 0.5 g, was added into this enzyme solution, and this mixture was shaken for one day to produce immobilization. Finally, this mixture was filtered to recover the immobilized lipase.

Test on Activity

Each 120 mg of these prepared immobilized lipase examples 1 to 3 and comparative examples 4 to 9 was added into the mixed solution of DL-1-phenethyl alcohol 1.2 ml and vinyl acetate 4.6 ml to perform esterification reaction. The relation between the initial activity (U/g) and the amount of protein adsorbed to the carriers (mg/g-carrier) after 20 min. from the beginning of esterification is shown in FIG. 1. The activity, 1 Unit (U), represents the amount of enzyme which generates phenethyl ester 1 μmol for one min.

In FIG. 1, the initial activities of three materials encircled A correspond to the three examples according to the present invention using the ester-combined immobilized lipase in which lipase is carried on the carrier combined with the silane coupling agent having carboxylic-ester linkage, No. 1 to No. 3, γ-methacryl oxypropyltrimethoxy silane, γ-acetoxypropyltrimethoxy silane or γ-acryloxypropyltrimethoxy silane. These three examples provide extremely high initial activity in comparison with the six comparative examples which are produced by using the other silane coupling agents, No. 4 to No. 9 and non-treated example without silane coupling agent, regardless of the amount of protein adsorbed to the carrier. For example, when the examples 1 to 3 are compared with the comparative example 9 which has substantially the same amount of adsorbed protein as these examples, the activity values of these three examples 1 to 3 encircled A are extremely higher than the comparative example 9 treated with phenethyltrimethoxy silane. On the other hand, when the examples 1 to 3 are compared with the comparative example 4 which has a great amount of adsorbed protein than the examples 1 to 3, the activity values of these three examples 1 to 3 are extremely higher than the comparative example 4 treated with allyltrimethoxy silane.

Batch Reaction Test

Batch reaction using the carrier (example 1) treated with γ-methacryl oxypropyltrimethoxy silane, No. 1, was repeated 30 times. As a reference, two type batch reactions using two carriers treated with allyltrimethoxy silane, No. 4, and non-treated were respectively repeated 30 times. The result of this batch reaction test is shown in FIG. 2 to clearly provide the relation between the change of activity (U/g) and the number of batch-reaction (repetition times) using the carriers of the example according to the present invention and that of the comparative example and non-treated carrier.

Figure 2:
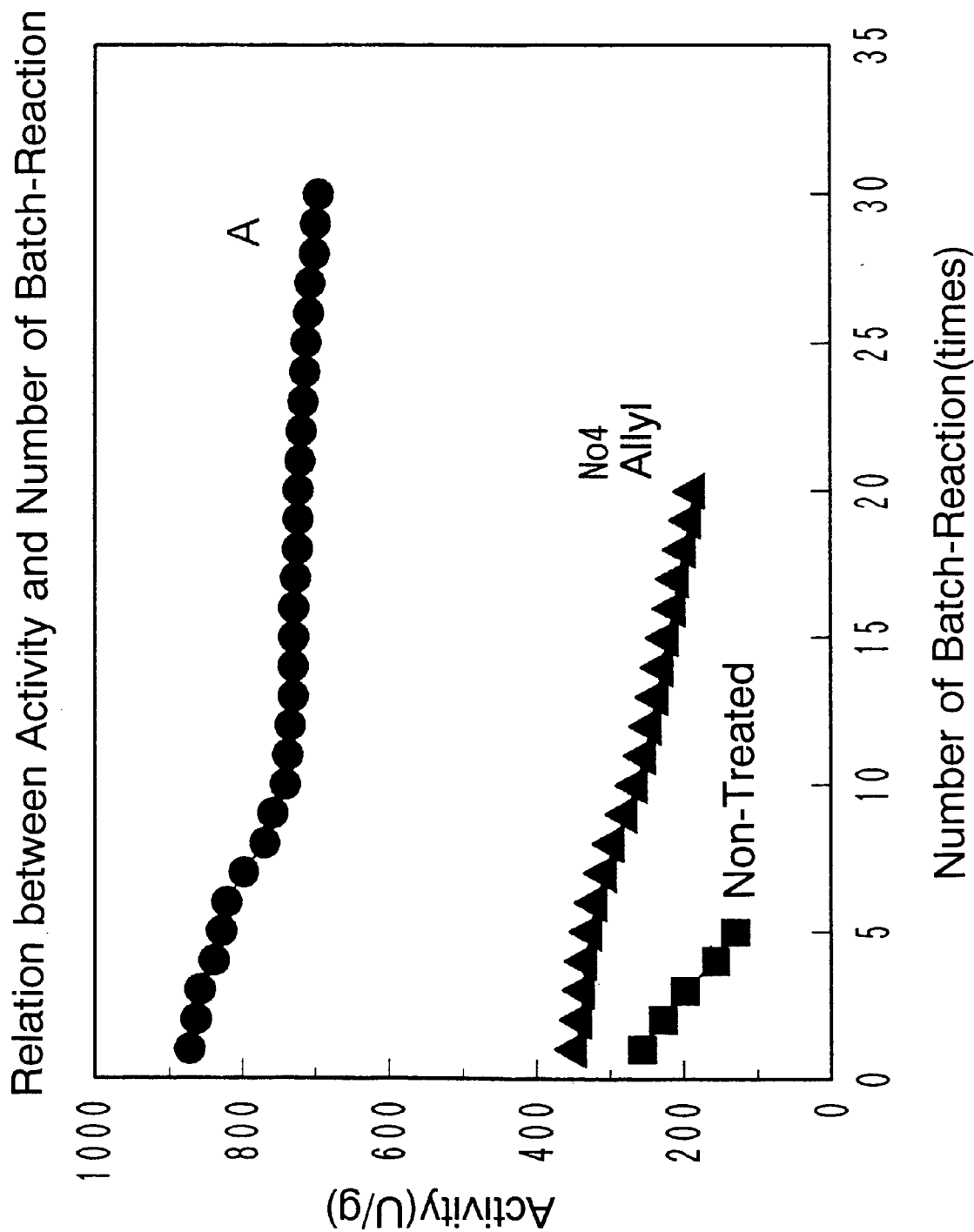
FIG. 2 is a graphical representation which shows the relation between the change of activity and the number of batch-reaction repeated using the carrier embodied in the present invention and that of the comparative example and non-treated carrier.

In FIG. 2, the example according to the present invention represented by "A" shows that the activity is slightly decreased by ten times and maintained at the substantially same level for 30 times after that. On the contrary, the comparative example 4 and non-treated example show that their activity are remarkably low in the beginning, and gradually decreased as the batch reaction was repeated.

Next, the kaolinite type carrier for immobilizing enzyme used for the above described examples 1 to 3 and another inorganic carrier such as commercial available glass beads (average particle diameter: 500 μm) were respectively treated with two treatments one of which used γ-methacryl oxypropyltrimethoxy silane, No. 1, and the other of which used allyltrimethoxy silane, No. 4, as comparative examples. These samples were subjected to the immobilizing treatment for lipase and esterification treatment in the same manner as the above described examples 1 to 3. Table 2 shows the resulting data representing the amount of adsorbed protein (mg/g), the initial ability (U/g) and the relative activity (U/mg) of the initial activity/the amount of adsorbed protein, for non-treated carrier, the example according to the present invention, and the comparative example.

TABLE 2

Comparison between Kaolinite Type Carrier for Immobilizing Enzyme and Glass Beads

| Sample | Silane Coupling Agent | Amount of Adsorbed Protein (mg/g) | Initial Activity (U/g) | Relative Activity (U/mg) |
|---|---|---|---|---|
| kaolinite type carrier | Non-treated | 39.5 | 254 | 6.4 |
| | allyltrimethoxy silane | 39.1 | 348 | 8.9 |
| | γ-methacryl oxypropyltrimethoxy silane | 33.2 | 873 | 26.3 |
| glass beads | Non-treated | 7.6 | 48 | 6.3 |
| | allyltrimethoxy silane | 7.2 | 64 | 8.9 |

TABLE 2-continued

Comparison between Kaolinite Type Carrier for Immobilizing Enzyme and Glass Beads

| Sample | Silane Coupling Agent | Amount of Adsorbed Protein (mg/g) | Initial Activity (U/g) | Relative Activity (U/mg) |
|---|---|---|---|---|
| | γ-methacryl oxypropyltrimethoxy silane | 5.7 | 150 | 26.3 |

As is clear from the resulting data shown in Table 2, the embodied sample according to the present invention has an extremely high initial activity even though the amount of protein adsorbed to the carrier is not as much as the comparative sample and non-treated sample. In detail, in the case of kaolinite type carrier for immobilizing enzyme, the amount of protein adsorbed to the non-treated carrier is 39.5 mg/g, to the comparative sample (treated with allyltrimethoxy silane) is 39.1 mg/g, and to the embodied sample (treated with γ-methacryl oxypropyltrimethoxy silane) is 33.2 mg/g. The non-treated sample and comparative sample are greater than the present invention. On the contrary, the initial activity of the embodied sample is 873 U/g, the non-treated sample is 254 U/g, and the comparative sample is 348 U/g. The embodied sample shows an extremely high value. Also, the relative activity of the non-treated sample is 6.4 U/mg, the comparative sample is 8.9 U/mg, and the embodied sample is 26.3 U/mg. The embodied sample also shows an extremely high value.

In the case of using commercial available glass beads as an inorganic carrier, the embodied sample has an extremely high initial activity, 150 U/g, even though the amount of protein adsorbed to the carrier is less than the comparative sample and non-treated sample. Furthermore, the relative activity of the embodied sample is 26.3 U/mg which is extremely higher than the other samples. This high value is equivalent to that of the kaolinite type carrier. Regardless of the kind of carrier material, it is confirmed that the coupling agent having carboxylic-ester linkage causes the carrier to have a high activity even though the amount of protein adsorbed to the carrier is not as much as the conventional samples. In other words, commercial available glass beads carrier has a low activity value rather than the kaolinite type carrier, but their relative activity values are equivalent, higher than the non-treated and comparative carrier samples. This means that the effect owing to the silane coupling agent having carboxylic-ester linkage is not only limited to a specific type of inorganic carrier material.

As given an the explanation above, the carrier and immobilized lipase produced by the present invention have an extremely high activity (relative activity) even though the amount of protein adsorbed to the carrier is not as much as in the conventional manner where lipase is carried with other carriers combined with the silane coupling agents having no carboxylic-ester linkage or non-treated carriers. Furthermore, the produced carriers and immobilized lipase can be repeatly used with hardly lowering its activity. Particularly, in repeating batch-reaction process, the produced carriers and immobilized lipase according to the present invention can be advantageously used for a long period.

As apparent, many widely different embodiments of this invention may be made without departing from the spirit and scope thereof, it is to be understood that the invention is not limited to the specific embodiment thereof as defined in the appended claims.

What is claimed:

1. An enzyme immobilizing carrier to immobilize lipase, comprising an inorganic carrier for carrying lipase, wherein said inorganic carrier is bonded to a silane coupling agent having a carboxylic-ester group.

2. The enzyme immobilizing carrier as set forth in claim 1, wherein said silane coupling agent having a carboxylic-ester group is represented by a general formula RCOO $(CH_2)_n$ $SiR'_3$ represents an organic functional group, R' represents a radical selected from the group including lower alkoxy, phenoxy, and halogen, and n represents an integral number.

3. The enzyme immobilizing carrier as set forth in claim 1, wherein said silane coupling agent having a carboxylic-ester group is selected from any one of γ-methacryl oxypropyltrimethoxy silane, γ-acetoxypropyltrimethoxy silane, and γ-acryloxypropyltrimethoxy silane.

4. The enzyme immobilizing carrier as set forth in claim 1, wherein said inorganic carrier is selected from any carriers having a functional group capable of combining with said silane coupling agent.

5. The enzyme immobilizing carrier as set forth in claim 1, wherein said inorganic carrier is selected from the group consisting of kaolinite, porous glass, bentonite, silica gel, alumina, silica, silica-alumina hydroxy apatite, and calcium phosphate-gel.

6. A method of making an immobilized lipase comprising the steps of:

a) bonding a silane coupling agent having a carboxylic-ester group to an inorganic carrier;

b) mixing and stirring the inorganic carrier with a lipase solution having a predetermined concentration to obtain a mixture;

c) filtering the mixture to obtain a filtered material; and d) drying the filtered material, wherein functional groups contained in the lipase protein are bonded to the carboxylic-ester group.

* * * * *